(12) United States Patent
Hotta

(10) Patent No.: US 9,188,532 B2
(45) Date of Patent: Nov. 17, 2015

(54) INSPECTION APPARATUS

(71) Applicant: FUJI XEROX CO., LTD., Tokyo (JP)

(72) Inventor: Hiroyuki Hotta, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 70 days.

(21) Appl. No.: 14/278,847

(22) Filed: May 15, 2014

(65) Prior Publication Data

US 2015/0092193 A1    Apr. 2, 2015

(30) Foreign Application Priority Data

Oct. 2, 2013    (JP) ................................. 2013-207620

(51) Int. Cl.
     *G01N 21/55*        (2014.01)

(52) U.S. Cl.
     CPC ..................................... *G01N 21/55* (2013.01)

(58) Field of Classification Search
     USPC ......... 356/445, 237.1–237.5; 250/201.5, 216, 250/221
     See application file for complete search history.

(56) References Cited

U.S. PATENT DOCUMENTS

| | | | | |
|---|---|---|---|---|
| 6,730,896 | B1 * | 5/2004 | Yamada | G02B 27/0068 250/201.5 |
| 7,157,703 | B2 * | 1/2007 | Nakasuji | H01J 37/28 250/311 |
| 2006/0043307 | A1 * | 3/2006 | Kimura | G01N 21/6428 250/370.01 |
| 2006/0104419 | A1 * | 5/2006 | Sasayama | G01N 23/207 378/145 |
| 2014/0097334 | A1 * | 4/2014 | Hotta | G01V 8/20 250/221 |

FOREIGN PATENT DOCUMENTS

| | | |
|---|---|---|
| JP | A-11-108636 | 4/1999 |
| JP | A-2003-156319 | 5/2003 |
| JP | A-2007-147316 | 6/2007 |

* cited by examiner

*Primary Examiner* — Sang Nguyen
(74) *Attorney, Agent, or Firm* — Oliff PLC

(57) ABSTRACT

An inspection apparatus includes a light emitting device, a first lens, a second lens, a light receiving device, and an inspection device. The light emitting device emits a light beam. The first lens is disposed such that an optical axis thereof extends in one direction and changes divergence of the light beam having been emitted from the light emitting device and passing therethrough. The second lens is disposed such that an optical axis of the second lens extends in the one direction. The light beam having exited the first lens and passing through the second lens is condensed on the inspection object by the second lens. The light receiving device is disposed between the first lens and the second lens and receives at least part of the reflected light beam. The inspection device detects a reflection characteristic in accordance with a result of light reception.

3 Claims, 13 Drawing Sheets

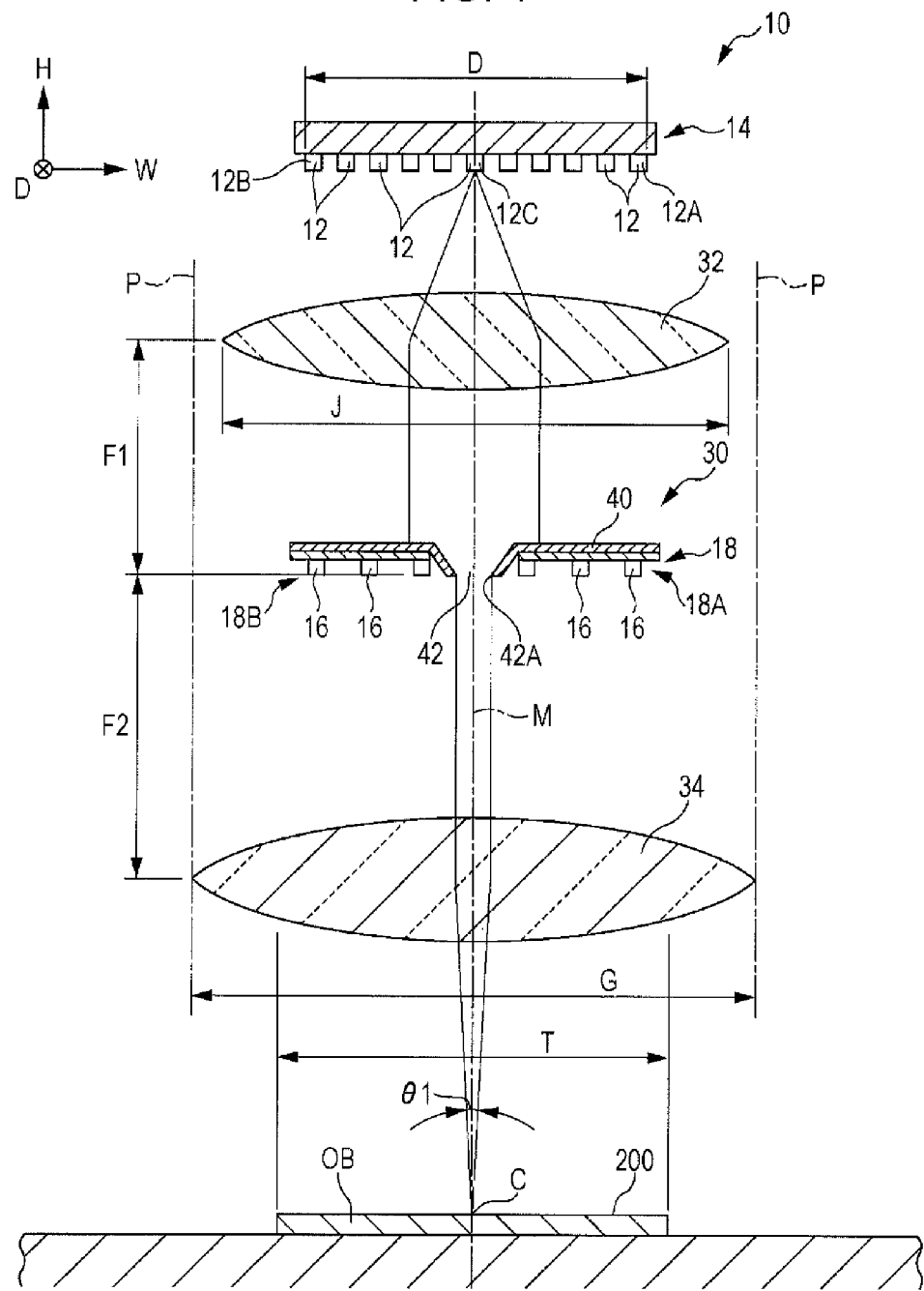

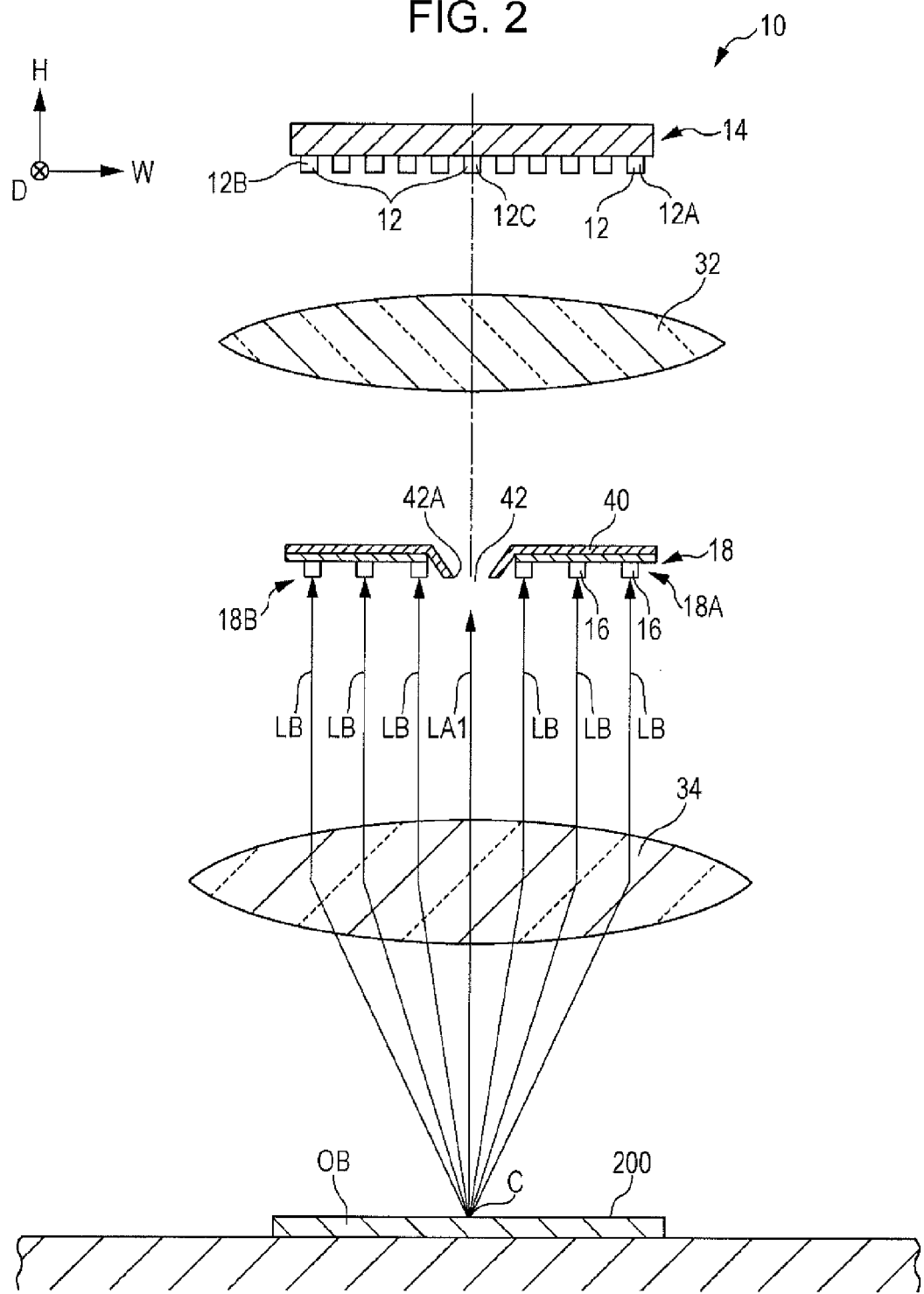

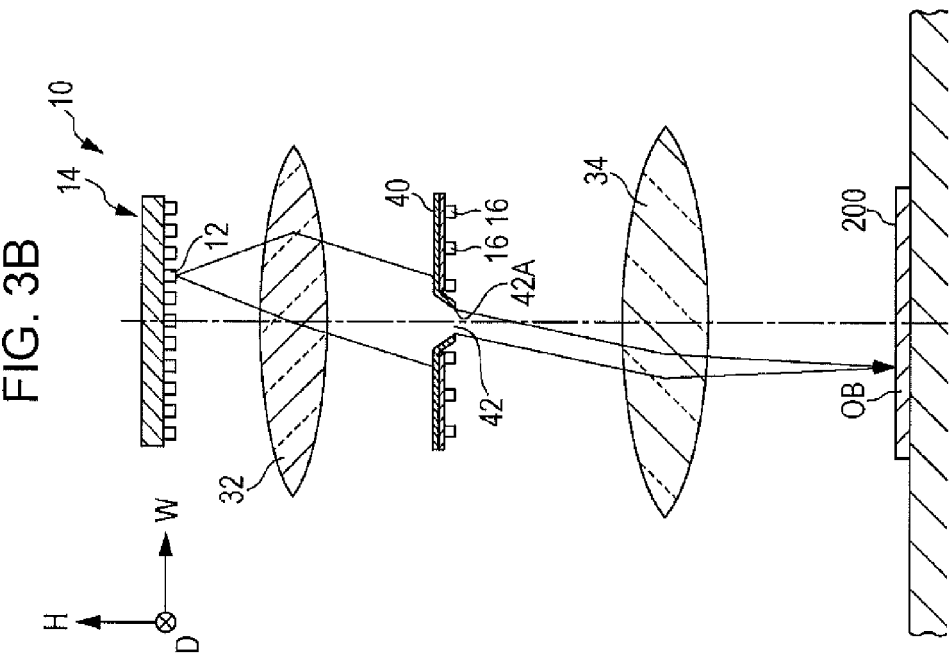
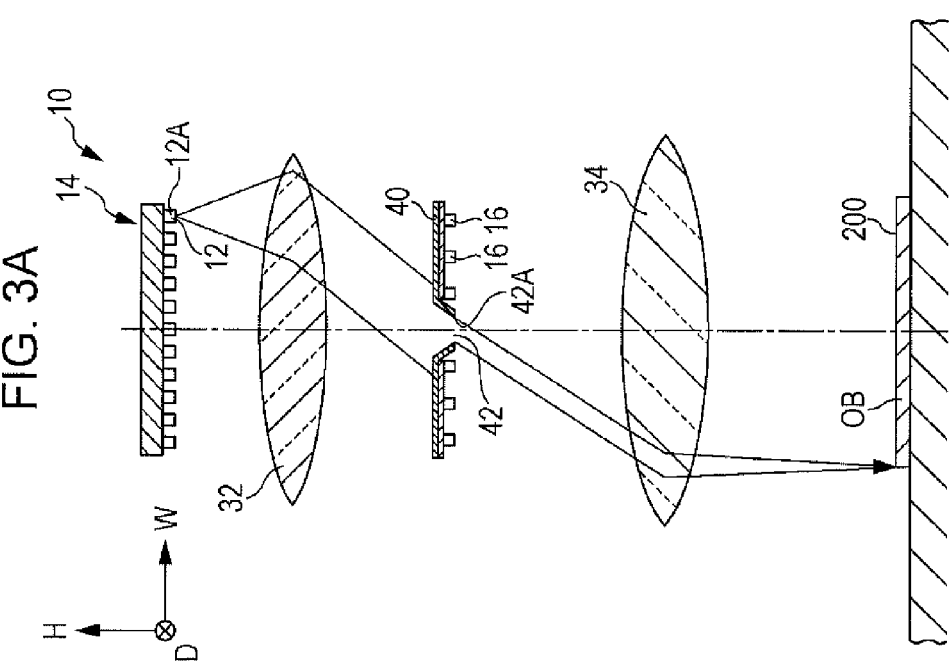

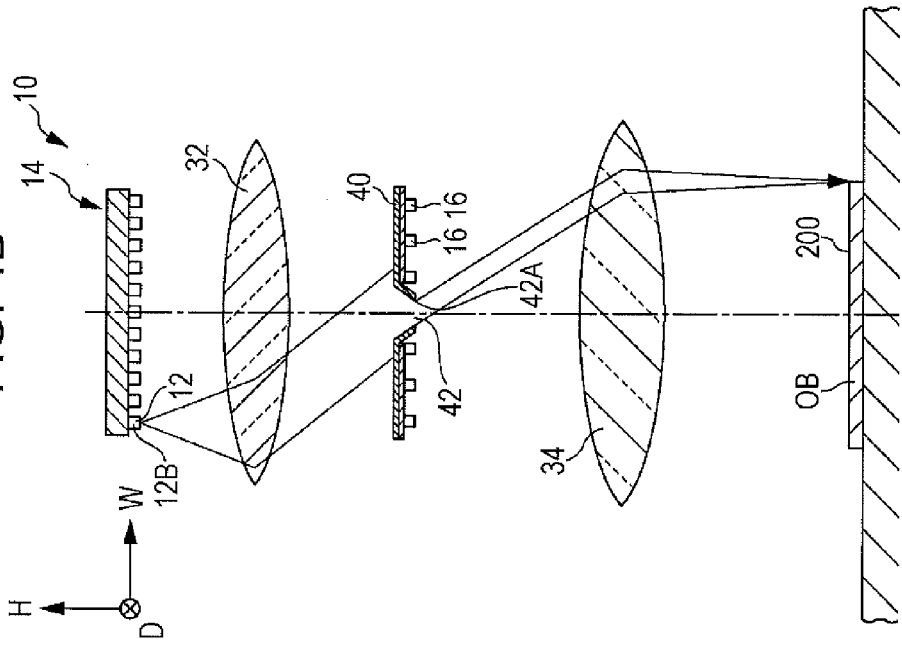
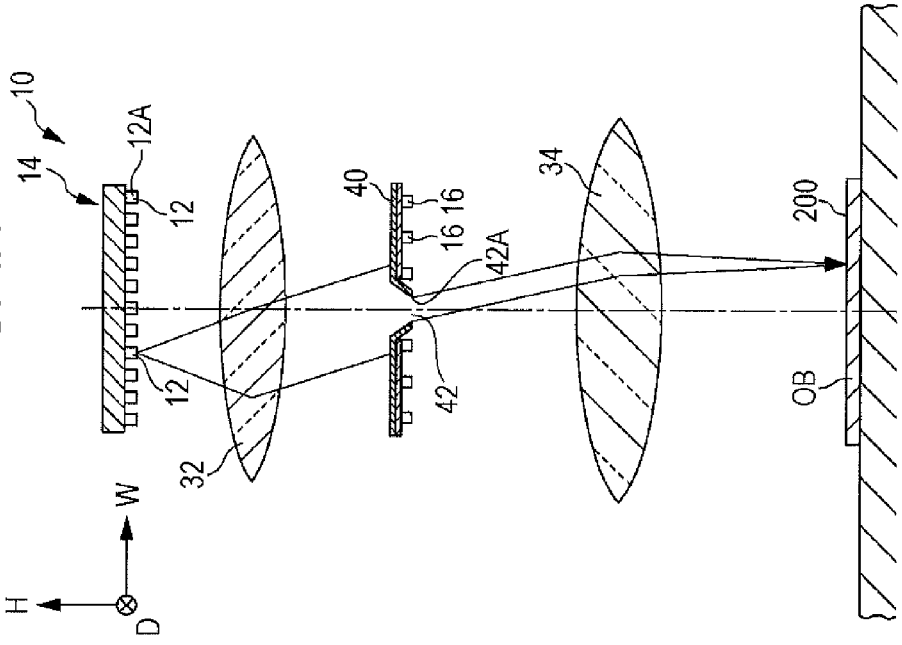

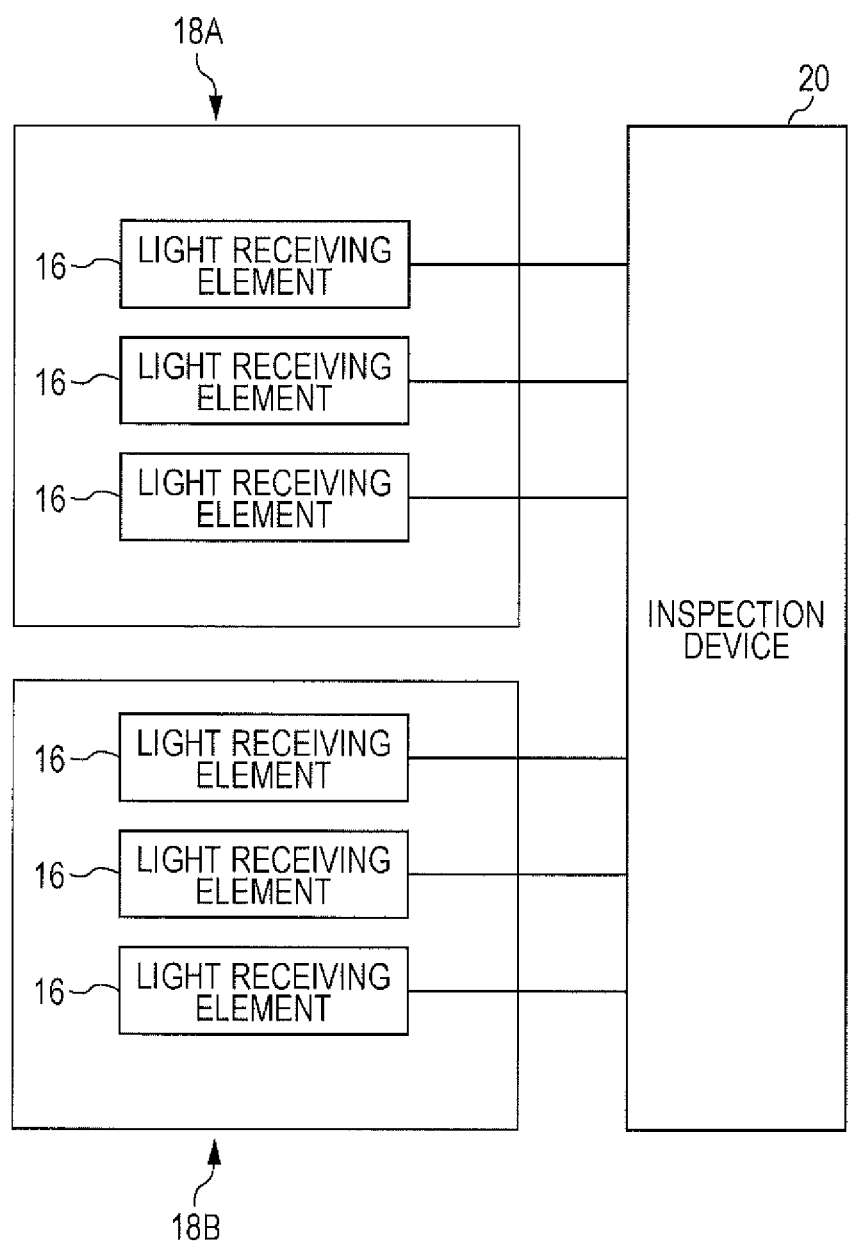

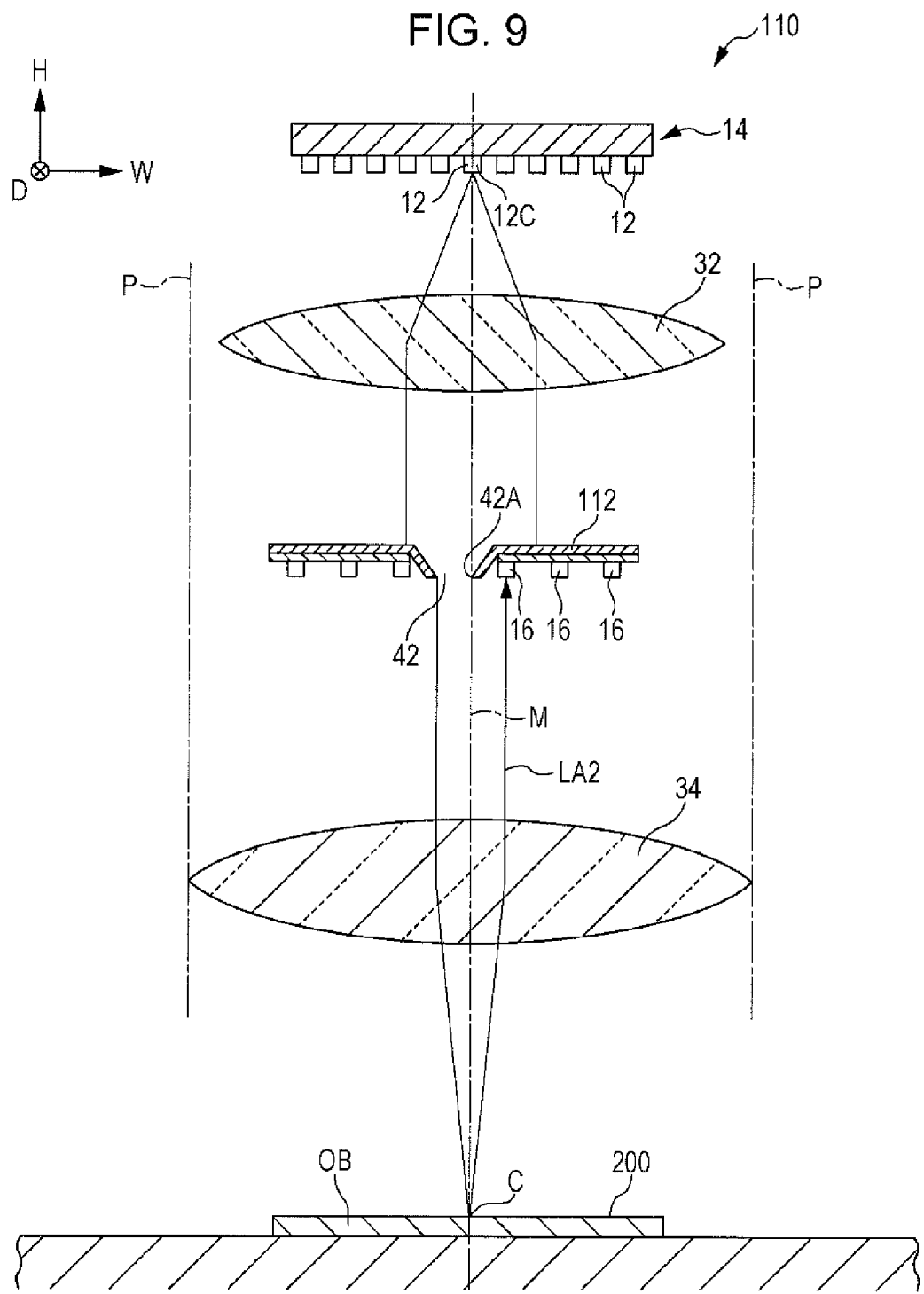

INSPECTION APPARATUS

CROSS-REFERENCE TO RELATED APPLICATIONS

This application is based on and claims priority under 35 USC 119 from Japanese Patent Application No. 2013-207620 filed Oct. 2, 2013.

BACKGROUND

Technical Field

The present invention relates to an inspection apparatus.

SUMMARY

According to an aspect of the present invention, an inspection apparatus that inspects an inspection object includes a light emitting device, a first lens, a second lens, a light receiving device, and an inspection device. The light emitting device emits a light beam. The first lens is disposed such that an optical axis of the first lens extends in one direction. The first lens changes divergence of the light beam that has been emitted from the light emitting device and passes through the first lens. The second lens is disposed such that an optical axis of the second lens extends in the one direction. The light beam that has exited the first lens and passes through the second lens is condensed on the inspection object by the second lens. The light receiving device is disposed between the first lens and the second lens and receives at least part of the light beam that has exited the second lens, been reflected by the inspection object, and passed through the second lens. The inspection device detects a reflection characteristic of at least part of the inspection object in accordance with a result of light reception performed by the light receiving device.

BRIEF DESCRIPTION OF THE DRAWINGS

Exemplary embodiments of the present invention will be described in detail based on the following figures, wherein:

FIG. 1 is a schematic diagram illustrating a configuration of an inspection apparatus according to a first exemplary embodiment of the present invention;

FIG. 2 is a schematic diagram illustrating a configuration of the inspection apparatus according to the first exemplary embodiment of the present invention;

FIGS. 3A and 3B illustrate the inspection apparatus according the first exemplary embodiment of the present invention and an inspection process in which an inspection object is inspected by the inspection apparatus;

FIGS. 4A and 4B illustrate the inspection apparatus according the first exemplary embodiment of the present invention and an inspection process in which an inspection object is inspected by the inspection apparatus;

FIG. 7 is a block diagram illustrating an inspection device and light receiving elements used in the inspection apparatus according the first exemplary embodiment of the present invention;

FIG. 9 is a schematic diagram illustrating a configuration of an inspection apparatus according to a third exemplary embodiment of the present invention;

DETAILED DESCRIPTION

First Exemplary Embodiment

Figure 5A:
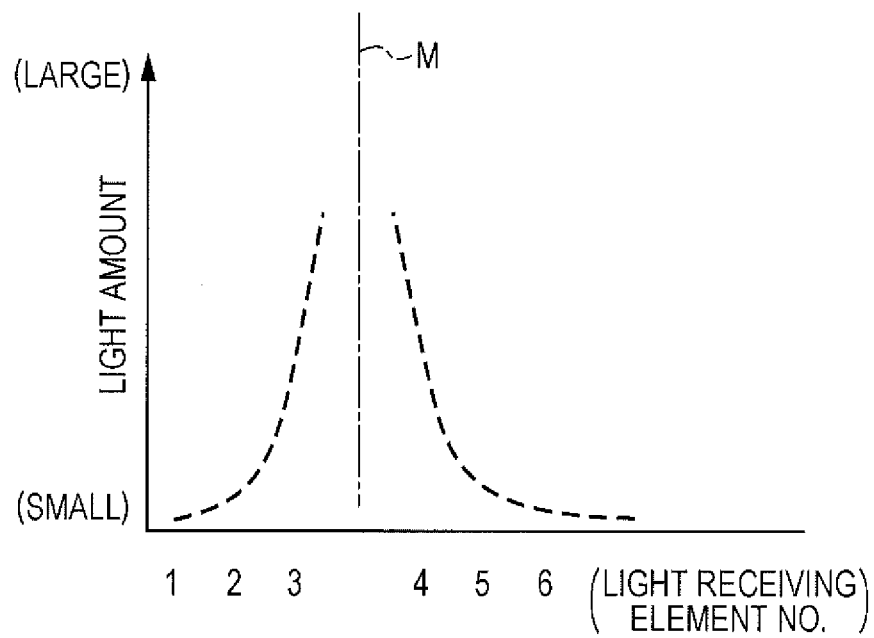
FIGS. 5A and 5B are graphs illustrating results of inspection performed by using the inspection apparatus according the first exemplary embodiment of the present invention.

An example of an inspection apparatus according to a first exemplary embodiment of the present invention is described with reference to FIGS. 1 to 7. In the drawings, an arrow H indicates an apparatus up-down direction (vertical direction), an arrow W indicates an apparatus width direction (horizontal direction), and an arrow D indicates an apparatus depth direction (horizontal direction).

Configuration

An inspection apparatus 10 according to the first exemplary embodiment radiates a light beam (pencil of light rays) to an inspection object OB, which is moved in the apparatus depth direction, so as to inspect reflection characteristics (for example, the reflection angle dependence of light amount distribution) of inspection object OB. As illustrated FIGS. 1 and 7, the inspection apparatus 10 includes a light emitting unit 14, a light receiving unit 18, and an inspection device 20. The light emitting unit 14 includes plural light sources 12 that each serve as an example of a light emitting device. The light receiving unit 18 includes plural light receiving elements 16 that each serve as an example of a light receiving device.

The inspection apparatus 10 also includes an optical system 30. The optical system 30 is disposed between the light emitting unit 14 and the inspection object OB and guides the light beam emitted from each of the light sources 12 to the inspection object OB.

Light Emitting Unit

As illustrated in FIG. 1, the light emitting unit 14 is disposed above an inspection region T in the apparatus up-down direction. The inspection object OB that is moved in the apparatus depth direction passes through the inspection region T. The plural light sources 12 of the light emitting unit 14 are mounted on a board, arranged in the apparatus width direction, and emit the light beams to the lower side in the apparatus up-down direction. Thus, the light sources 12 are arranged in a direction that (perpendicularly) intersects the movement direction (apparatus depth direction) of the inspection object OB.

Furthermore, the light sources 12 from a light source 12A disposed on one end side (right end in FIG. 1) to a light source 12B disposed on the other end side (left end in FIG. 1) in the apparatus width direction emit light beams to the inspection object OB with a time difference set between light beam emission from any one of these light sources 12 to light beam emission from the next one of the light sources 12. The light beam emission from the light sources 12 from the light sources 12A to 12B are repeated while the inspection object OB is being moved in the inspection region T.

Optical System

The optical system 30 uses a so-called bi-telecentric lens. As illustrated in FIG. 1, the optical system 30 includes a lens element 32 serving as an example of a first lens and a lens element 34 serving as an example of a second lens arranged in this order from the light emitting unit 14 side to the inspection object OB side. The optical system 30 also includes a stop member 40 serving as an example of a stop device disposed between the lens element 32 and the lens element 34. The stop member 40 restricts the light beam that pass therethrough.

The optical axis of the lens element 32 and the optical axis of the lens element 34 are similar to each other. The lens element 32 and the lens element 34 are arranged such that an optical axis M of the lens element 32 and the lens element 34 extends in the apparatus up-down direction (an example of one direction). Furthermore, a light source 12C arranged at the center in the above-described light sources 12 in the apparatus width direction is disposed on the optical axis M.

The lens element 32 uses a convex lens having a circular shape in plan view. The dimension of the lens element 32 in the apparatus width direction (dimension J in FIG. 1) is greater than the distance between the light source 12A and the light source 12B (distance D in FIG. 1) in the apparatus width direction. Thus, the light beam emitted from each of the light sources 12 passes through the lens element 32. This changes the divergence of the light beam passing through the lens element 32 so as to collimate the light beam into parallel light directed to the lens element 34.

Likewise, the lens element 34 uses a convex lens having a circular shape in plan view. The dimension of the lens element 34 in the apparatus width direction (dimension G in FIG. 1) is greater than the dimension the lens element 32 in the apparatus width direction. The light beam having exited from the lens element 32 and passing through the lens element 34 is condensed on the inspection object OB by the lens element 34.

The stop member 40 is disposed between the lens element 32 and the lens element 34 and has a circular aperture 42 so as to restrict the light beam having passed through the lens element 32 and to be incident upon the lens element 34. Specifically, the stop member 40 has a plate shape, plate surfaces of which face the apparatus up-down direction. A tip end portion is formed in the stop member 40. The tip end portion is formed by bending part of the stop member 40 around the optical axis M toward the lens element 34 so as to be tapered toward the lens element 34. This tip end portion serves as an aperture edge 42A that defines the aperture 42. The axis of the circular shape formed by the aperture 42 is the optical axis M.

In the apparatus up-down direction, the distance between the aperture edge 42A and the lens element 32 (F1 in FIG. 1) is substantially equal to the focal length of the lens element 32, and the distance between the aperture edge 42A and the lens element 34 (F2 in FIG. 1) is substantially equal to the focal length of the lens element 34.

Light Receiving Unit

The light receiving unit 18 is disposed on the lower side of the stop member 40 between the lens element 32 and the lens element 34 in the apparatus up-down direction. The light receiving unit 18 includes a light receiving unit 18A and a light receiving unit 18B, which are respectively disposed on the right side and the left side of the optical axis M in FIG. 1.

Since the configurations of the light receiving unit 18A and the light receiving unit 18B are similar to each other, the light receiving unit 18A is described in most cases in the following.

The light receiving unit 18A includes the plural (three in FIG. 1) light receiving elements 16 mounted on a board and arranged in the apparatus width direction. As described above, since the light receiving unit 18 is disposed between the lens element 32 and the lens element 34, the light receiving elements 16 are disposed between the lens element 32 and the lens element 34.

Here, the details of arrangement of the light receiving elements 16 between the lens element 32 and the lens element 34 are as follows: as illustrated in FIG. 1, the light receiving elements 16 are disposed inside lines P (cylindrical surface) in the apparatus width direction, the lines P extending in the apparatus up-down direction and passing through ends of outer diameter (virtual points of contact where the radii of a front and rear surfaces are in contact with one another) of a lens (lens element 34 in the present exemplary embodiment) having a larger outer diameter than the other lens. In order to determine ends of the outer diameter, when the length of the radius of the front or rear surface is not uniform, the longest length is used.

Furthermore, the light receiving surfaces of the light receiving elements 16 and the aperture edge 42A are disposed at similar positions, and the distance between the lens element 34 and the light receiving surfaces of the light receiving elements 16 (optical path length: F2 in FIG. 1) is substantially equal to the focal length of the lens element 34.

Furthermore, in the apparatus depth direction, the light receiving elements 16 and the aperture 42 are disposed at similar positions. For this reason, in the apparatus width direction, it is impossible to dispose the light receiving elements 16 at the position of the aperture 42. Thus, in FIG. 1, the distance between the light receiving element 16 disposed at the left end of the light receiving unit 18A and the light receiving element 16 disposed at the right end of the light receiving unit 18B is larger than the distance between the other light receiving elements 16. In other words, the light receiving element 16 that may otherwise be disposed between the light receiving unit 18A and the light receiving unit 18B is missing.

In this configuration, the light receiving elements 16 receive at least part of the light beam (see diverted light LB in FIG. 2), which have exited the lens element 34, have been reflected by the inspection object OB, and have passed through the lens element 34.

Inspection Device

As illustrated in FIG. 7, the inspection device 20 receives results of light reception performed by the light receiving elements 16. The inspection device 20 detects the reflection characteristics of the inspection object OB in accordance with the results of light reception performed by the light receiving elements 16.

Operation

Next, operations of the inspection apparatus 10 are described with an example case where the inspection apparatus 10 inspects the reflection characteristics (for example, degree of irregularity of the surface) of the plate-shaped inspection object OB. In FIGS. 1, 3A, 3B, 4A, and 4B, the light beam radiated to the inspection object OB is illustrated. In FIG. 2, the light beam reflected by the inspection object OB is illustrated.

Initially, when the inspection object OB is moved in the apparatus depth direction, and a front end of the inspection object OB enters the inspection region T, as illustrated in FIGS. 3A, 3B, 4A, and 4B, the light sources 12 from the light source 12A disposed on the one end side to the light source 12B disposed on the other end side in the apparatus width direction emit light beams to the inspection object OB with a time difference set between light beam emission from any one of these light sources 12 to light beam emission from the next one of the light sources 12. The light beam emission from the light sources 12 from the light sources 12A to 12B are repeated until a rear end of the inspection object OB is moved out of the inspection region T.

The lens element 32 changes the divergence of the light beam having been emitted from each of the light sources 12 and passing therethrough so as to direct the light beam to the lens element 34. The stop member 40 restricts the light beam, the divergence of which has been changed by the lens element 32. The lens element 34 condenses the light beam having been restricted by the stop member 40 and being incident thereupon and causes the light beam to exit so that the inspection object OB is irradiated with the light beam in the apparatus up-down direction (optical axis direction).

The light beam, with which the inspection object OB is irradiated, is reflected by a surface 200 of the inspection object OB. The lens element 34 changes the divergence of the light beam having been reflected by the inspection object OB and passing therethrough (referred to as a "reflected light beam" hereafter) so as to direct the light beam to the light receiving elements 16. The light receiving elements 16 receive the reflected light beam having passed through the lens element 34. The inspection device 20 detects the degree of irregularity of the inspection object OB in accordance with the results of light reception performed by the light receiving elements 16. It is noted that, as illustrated in FIGS. 1 and 2, specular reflection light LA1 (see FIG. 2) having been emitted from the light source 12C and specularly reflected at a central portion C of the surface 200 of the inspection object OB, the central portion C being substantially at the center in the apparatus width direction, is not received by the light receiving elements 16 because the specular reflection light LA1 passes through the aperture 42 after having passed through the lens element 34. In other words, the result of reception of the specular reflection light LA1 at the central portion C is not obtainable.

Figure 6A:
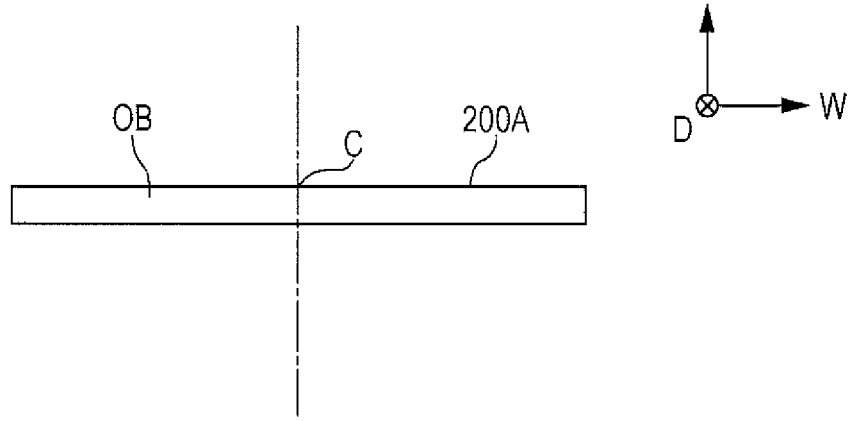
FIGS. 6A and 6B are side views of inspection objects to be inspected by the inspection apparatus according the first exemplary embodiment of the present invention.
Figure 6B:
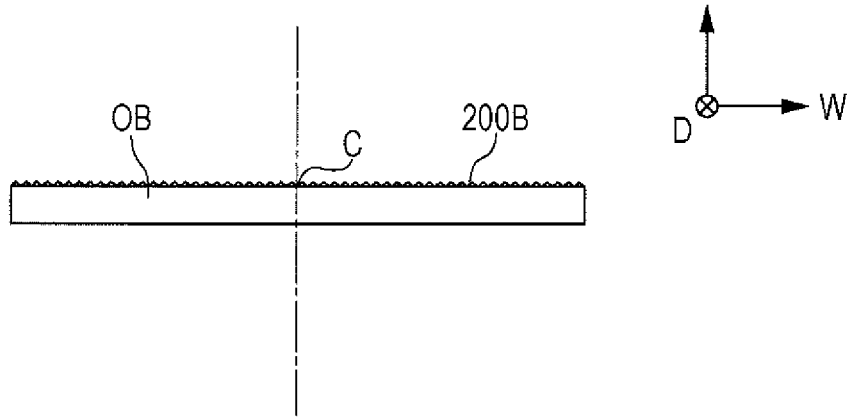

Here, inspection results (detection results) of a surface 200A and a surface 200B obtained by the inspection device 20 are described. The surfaces 200A and 200B are types of the surface 200 of the inspection object OB having different degrees of irregularity. As illustrated in FIGS. 6A and 6B, the degree of irregularity of the surface 200A is smaller than that of the surface 200B.

Figure 5B:
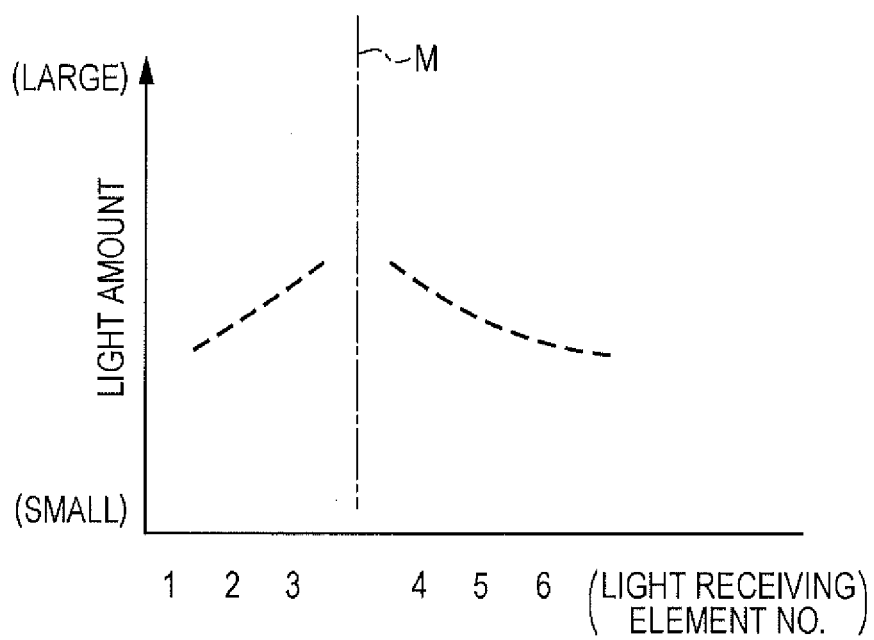

FIGS. 5A and 5B are graphs respectively illustrating the inspection results of the central portions C of the surface 200A and the surface 200B, the central portions C being substantially at the center in the apparatus width direction.

In each of the graphs illustrated in FIGS. 5A and 5B, numbers of the light receiving elements 16 are indicated along the horizontal axis. The numbers 1 to 6 of the light receiving elements 16 are sequentially assigned from the left on the page of each of the drawings. That is, the numbers assigned to the light receiving elements 16 of the light receiving unit 18B are 1 to 3, and the numbers assigned to the light receiving elements 16 of the light receiving unit 18A are 4 to 6. In each of the graphs illustrated in FIGS. 5A and 5B, the vertical axis indicates the magnitude of the light amount of reflected light beam received by the light receiving elements 16.

As illustrated in FIG. 5A, regarding the results of the surface 200A, the degree of irregularity of which is small, the light amount of the specular reflection light LA1 (referred to as "specular reflection component" hereafter) is larger than the light amount of divergent reflected light component (referred to as "divergent reflection component" hereafter). Thus, the curves are steep. In contrast, as illustrated in FIG. 5B, regarding the results of the surface 200B, the degree of irregularity of which is large, the ratio of the specular reflection component to the divergent reflection component is smaller than that of the surface 200A. Thus, the curves are gentle.

As has been described above, since the light receiving elements 16 are disposed between the lens element 32 and the lens element 34, the size of the inspection apparatus 10 is reduced compared to the case where the light receiving elements 16 are disposed at positions other than the positions between the lens element 32 and the lens element 34.

The divergence of the reflected light beam is changed by the lens element 34, which is used to condense the light beam on the inspection object OB, so that the reflected light beam is directed to the light receiving elements 16. Thus, the number of components is reduced compared to the case where a lens that condenses the light beam and a lens that changes the divergence are separately provided. The size of the inspection apparatus 10 is also reduced by this configuration.

Furthermore, in the apparatus up-down direction, the distance between the lens element 34 and the light receiving surfaces of the light receiving elements 16 (F2 in FIG. 1) is substantially equal to the focal length of the lens element 34. This suppresses degradation of accuracy of inspection of the reflection characteristics even when the position of the inspection object OB is moved up or down in the apparatus up-down direction.

Furthermore, in the apparatus up-down direction, the distance between the aperture edge 42A of the stop member 40 and the lens element 32 (F1 in FIG. 1) is substantially equal to the focal length of the lens element 32, and the distance between the aperture edge 42A and the lens element 34 (F2 in FIG. 1) is substantially equal to the focal length of the lens element 34. Thus, a radiation angle ($\theta 1$ in FIG. 1) of each of the light beams radiated from a corresponding one of the light sources 12 to the inspection object OB is specified.

Since the radiation angle of each of the light beams radiated from a corresponding one of the light sources 12 to the inspection object OB is specified, the specular reflection component and the divergent reflection component of the reflected light beam reflected by the surface 200B of the inspection object OB are quantitatively distributed at inspection points. This allows comparison of the inspection results among the inspection points.

Furthermore, since the radiation angle of each of the light beams radiated from a corresponding one of the light sources 12 to the inspection object OB is specified, the radiation angle may be reduced. This allows the light beam including the optical axis thereof to be narrowed.

Furthermore, since the stop member 40 restricts the light beam, the radiation angle is reduced. By reducing the radiation angle, a change in size of a radiation spot caused by variation of the inspection object OB in the height H direction is suppressed. Thus, variation in inspection range is suppressed.

The specular reflection light LA1 having been specularly reflected at the central portion C of the inspection object OB, the central portion C substantially at the center in the width direction, passes through the lens element 34 and the aperture 42. Thus, data corresponding to this portion is missing (see FIGS. 5A and 5B). However, the missing data may be estimated by comparing the light amount distribution of the light received by the light receiving elements 16.

Second Exemplary Embodiment

Figure 8:
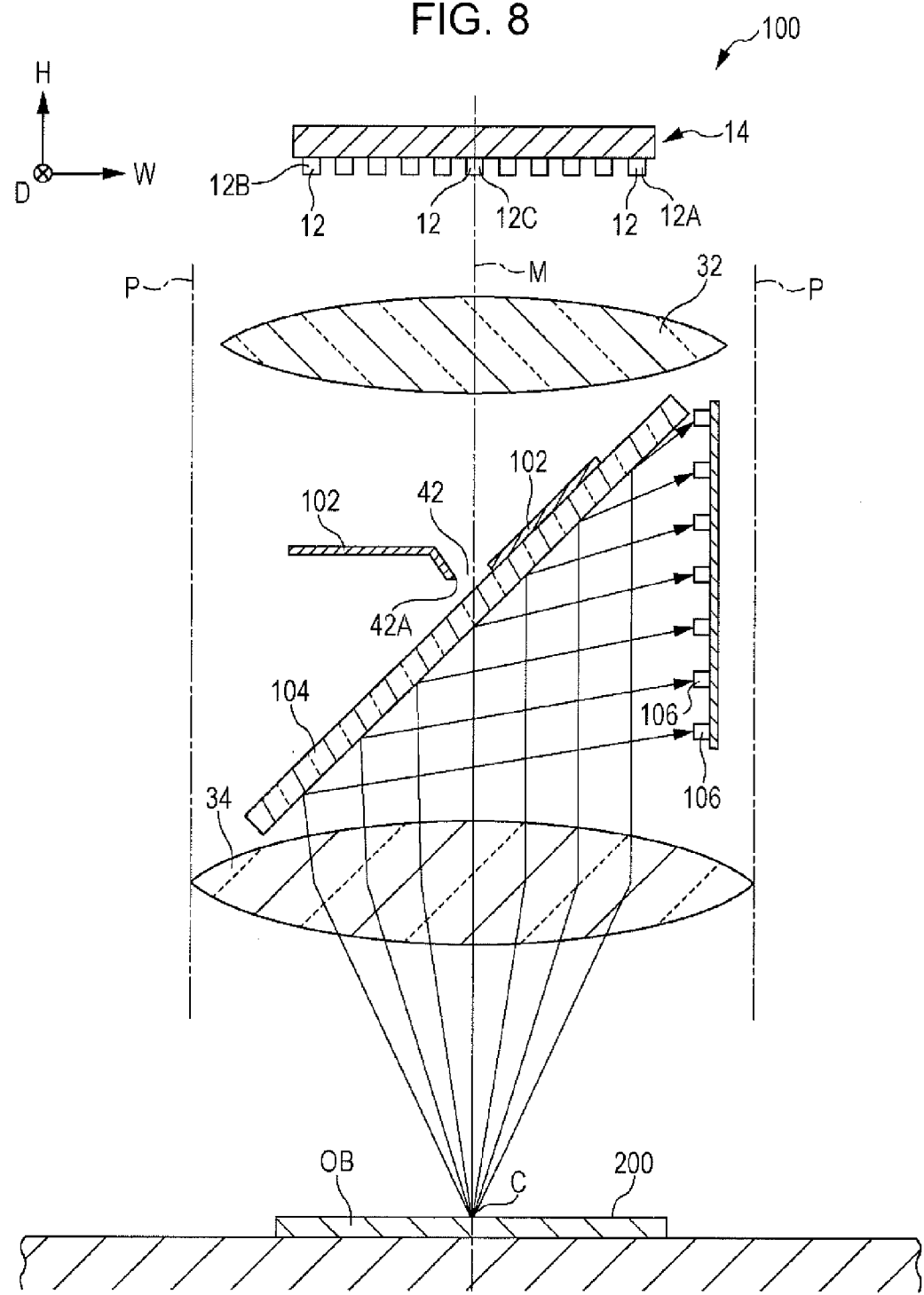
FIG. 8 is a schematic diagram illustrating a configuration of an inspection apparatus according to a second exemplary embodiment of the present invention.

An example of an inspection apparatus according to a second exemplary embodiment of the present invention is described with reference to FIG. 8. The same elements or the like as those in the first exemplary embodiment are denoted by the same reference signs and description thereof is omitted. Most of the following description is devoted to points different from those in the first exemplary embodiment. In FIG. 8, the reflected light beam, which is emitted from the light source 12C and reflected by the central portion C of the inspection object OB, is illustrated.

An inspection apparatus 100 according to the second exemplary embodiment includes a half mirror 104. The half mirror 104 reflects part of each light beam incident thereupon and allows the other part of the light beam incident thereupon to pass therethrough.

Specifically, as illustrated in FIG. 8, the half mirror 104 is disposed between the lens element 32 and the lens element 34 so as to reflect the reflected light beam, which has been reflected by the inspection object OB and passed through the lens element 34, to light receiving elements 106 arranged in the apparatus up-down direction. Here, arrangement of the light receiving elements 106 does not interfere with arrangement of the aperture 42. Thus, no light receiving element 106 is missing.

Furthermore, the distance (optical path length) between the lens element 34 and light receiving surfaces of the light receiving elements 106 is substantially equal to the focal length of the lens element 34.

The inspection apparatus 100 also includes a stop member 102 serving as an example of the stop device disposed between the lens element 32 and the half mirror 104. In order not to interfere with the half mirror 104, the right side of the stop member 102 in the page of FIG. 8 has a shape that conforms to a plate surface of the half mirror 104.

In the above-described configuration, the stop member 102 restricts the light beam, the divergence of which has been changed by the lens element 32. The half mirror 104 also causes part of the light beam having been restricted by the stop member 102 to pass therethrough and to be incident upon the lens element 34.

The light beam, with which the inspection object OB is irradiated, is reflected by the surface 200 of the inspection object OB. The lens element 34 changes the divergence of the reflected light beam having been reflected by the surface 200 of the inspection object OB and passing therethrough so as to direct the light beam to the half mirror 104. The half mirror 104 reflects part of the reflected light beam having passed through the lens element 34 to the light receiving elements 106. The light receiving elements 106 receive the reflected light beam reflected by the half mirror 104.

Although the light amount of the light beam is reduced when the light beam is caused to pass through or be reflected by the half mirror 104 as described above, arrangement of the light receiving elements 106 does not interfere with arrangement of the aperture 42. Thus, missing of data is suppressed. Other operations are similar to those in the first exemplary embodiment.

Third Exemplary Embodiment

An example of an inspection apparatus according to a third exemplary embodiment of the present invention is described with reference to FIGS. 9 and 10. The same elements or the like as those in the first exemplary embodiment are denoted by the same reference signs and description thereof is omitted. Most of the following description is devoted to points different from those in the first exemplary embodiment. In FIG. 9, in the reflected light beam, specular reflection light LA2 is illustrated.

As illustrated in FIG. 9, a stop member 112 that serves as an example of a stop device used in an inspection apparatus 110 according to the third exemplary embodiment is offset to the left side in FIG. 9 compared to that in the first exemplary embodiment. The aperture edge 42A of the stop member 112 is positioned in the optical axis M. That is, the aperture 42 of the stop member 112 is offset to the left side in FIG. 9 compared to that in the first exemplary embodiment.

In the above-described configuration, the lens element 34 condenses the light beam having been emitted from the light source 12C, passed through the lens element 32, and restricted by the stop member 112, and the inspection object OB is irradiated with this condensed light beam. Here, since the stop member 112 is offset to the left side in FIG. 9 compared to that in the first exemplary embodiment, the lens element 34 directs the light beam to the inspection object OB such that the central portion C of the inspection object OB is irradiated with the light beam from the left side in FIG. 9.

The light beam, with which the central portion C of the inspection object OB has been irradiated from the left side in FIG. 9, is reflected to the right side in FIG. 9. One of the light receiving elements 16 (the fourth light receiving element 16 from the left in FIG. 9) receives the specular reflection light LA2 having been specularly reflected at the central portion C.

Figure 10A:
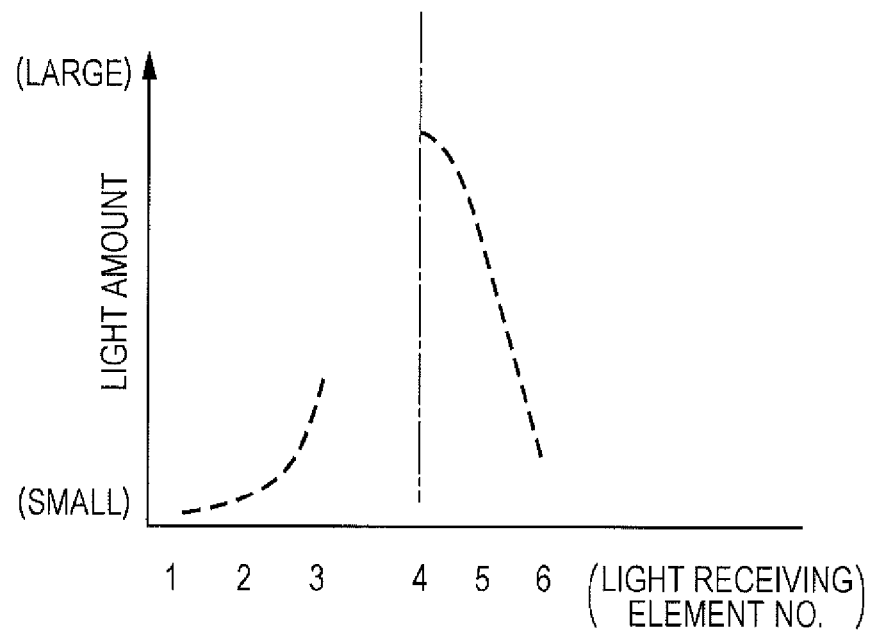
FIGS. 10A and 10B are graphs illustrating results of inspection performed by using the inspection apparatus according the third exemplary embodiment of the present invention.
Figure 10B:
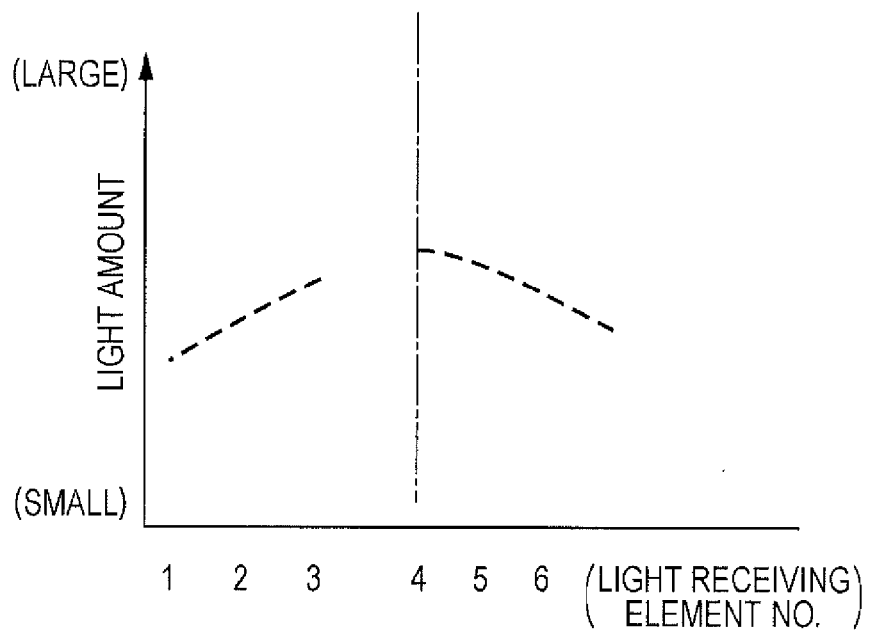

FIGS. 10A and 10B are graphs respectively illustrating the inspection results of the central portions C of the surface 200A and the surface 200B, the central portions C being substantially at the center in the apparatus width direction.

As illustrated in FIGS. 10A and 10B, the light amount of the specular reflection light LA2 is output. The specular reflection light LA2 is specularly reflected at the central portion C of the inspection object OB, the central portion C being substantially at the center in the apparatus width direction. Data of part of the divergent reflected light is missing. Other operations are similar to those in the first exemplary embodiment.

Fourth Exemplary Embodiment

An example of an inspection apparatus according to a fourth exemplary embodiment of the present invention is described with reference to FIG. 11. The same elements or the like as those in the third exemplary embodiment are denoted by the same reference signs and description thereof is omitted. Most of the following description is devoted to points different from those in the third exemplary embodiment.

In the third exemplary embodiment, the aperture 42 of the stop member 112 is offset to the left side in FIG. 9. Thus, in the light beam emitted from the light source 12C, a component of the light beam, the light amount of which is large (light near the center in the light beam), is restricted more by the stop member 112 than that in the first exemplary embodiment. For this reason, the light amount of the specular reflection light LA2 specularly reflected at the central portion C of the inspection object OB, the central portion C being substantially at the center in the apparatus width direction, is reduced.

Figure 11:
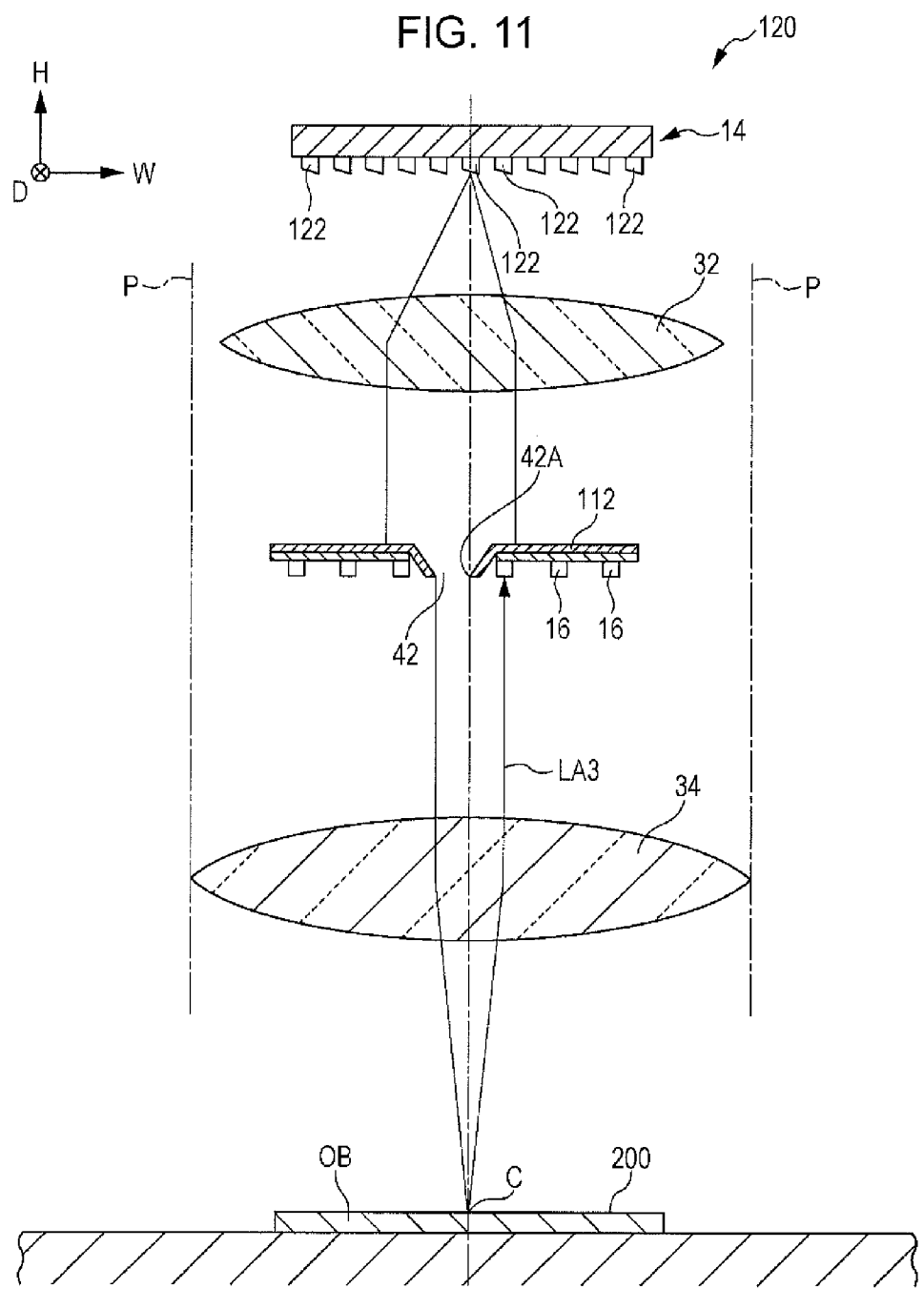
FIG. 11 is a schematic diagram illustrating a configuration of an inspection apparatus according to a fourth exemplary embodiment of the present invention.

Light sources 122 each serving as an example of the light emitting device of an inspection apparatus 120 according to a fourth exemplary embodiment are disposed so as to emit light beams that are inclined leftward in FIG. 11 relative to the apparatus up-down direction. Specifically, the light sources 122 are disposed so that, in the light beam emitted from the light source 12C, the component of the light beam, the light amount of which is large, is not restricted by the stop member 112.

Thus, reduction of the light amount of specular reflection light LA3 specularly reflected at the central portion C of the inspection object OB, the central portion C being substantially at the center in the apparatus width direction, is suppressed. Other operations are similar to those in the third exemplary embodiment.

Fifth Exemplary Embodiment

An example of an inspection apparatus according to a fifth exemplary embodiment of the present invention is described with reference to FIG. 12. The same elements or the like as those in the first exemplary embodiment are denoted by the same reference signs and description thereof is omitted. Most of the following description is devoted to points different from those in the first exemplary embodiment.

Figure 12:
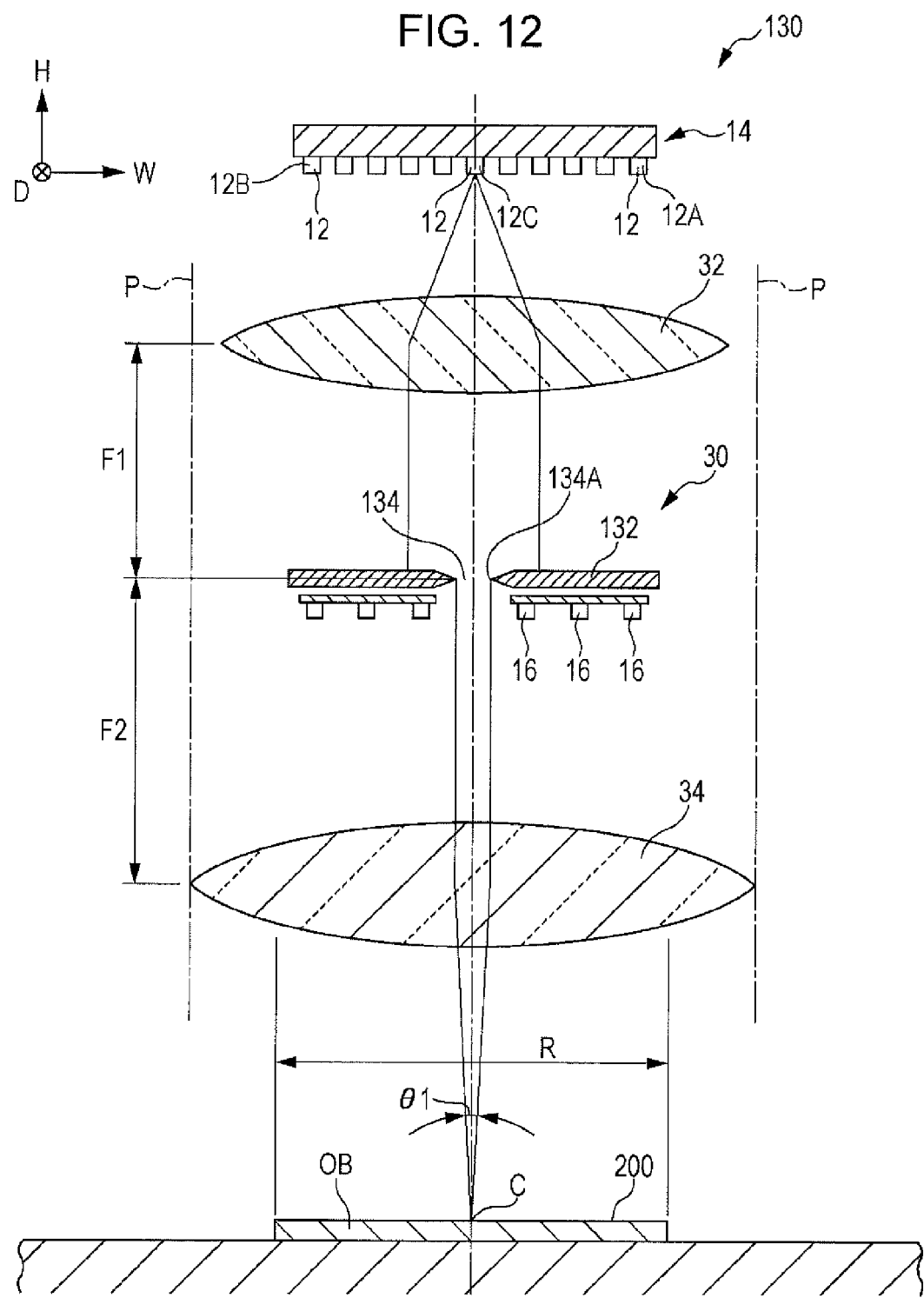
FIG. 12 is a schematic diagram illustrating a configuration of an inspection apparatus according to a fifth exemplary embodiment of the present invention.

As illustrated in FIG. 12, a stop member 132 used in an inspection apparatus 130 according to the fifth exemplary embodiment has a plate shape, plate surfaces of which face the apparatus up-down direction. A circular aperture 134 is formed in the stop member 132. Specifically, the stop member 132 has no bent portion. The thickness of a portion of the stop member 132 is gradually reduced, and the end of the reduced portion forms an aperture edge 134A, by which the aperture 134 is defined.

In the apparatus up-down direction, the distance between the aperture edge 134A and the lens element 32 (F1 in FIG. 12) is substantially equal to the focal length of the lens element 32, and the distance between the aperture edge 134A and the lens element 34 (F2 in FIG. 12) is substantially equal to the focal length of the lens element 34.

The light receiving elements 16 are arranged in the apparatus width direction on the lens element 34 side of the stop member 132 in the apparatus up-down direction.

Operations in the fifth exemplary embodiment are similar to those in the first exemplary embodiment except for the following operation: the operation that may be performed because the distance between the light receiving surfaces of the light receiving elements 16 and the lens element 34 in the apparatus up-down direction is substantially equal to the focal length of the lens element 34.

Sixth Exemplary Embodiment

An example of an inspection apparatus according to a sixth exemplary embodiment of the present invention is described with reference to FIG. 13A. The same elements or the like as those in the first exemplary embodiment are denoted by the same reference signs and description thereof is omitted. Most of the following description is devoted to points different from those in the first exemplary embodiment.

Figure 13A:
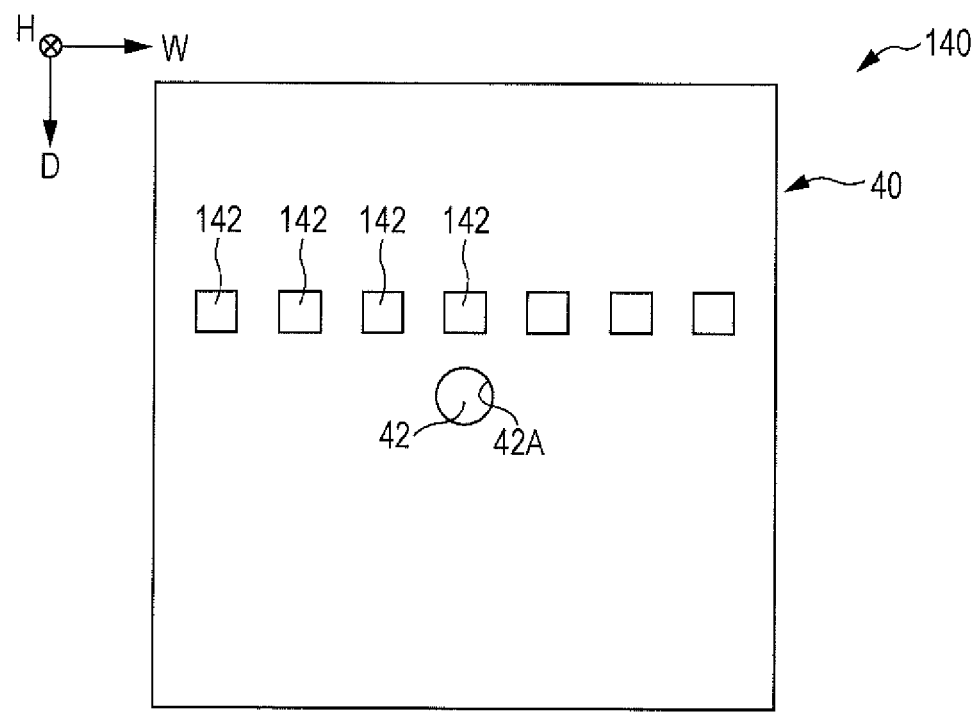
FIGS. 13A and 13B are bottom views illustrating light receiving elements used in inspection apparatuses according sixth and seventh exemplary embodiments of the present invention.

As illustrated in FIG. 13A, light receiving elements 142 that each serve as an example of the light receiving device used in an inspection apparatus 140 according to the sixth exemplary embodiment are offset in the apparatus depth direction relative to the aperture 42 of the stop member 40. Thus, in the apparatus width direction, the light receiving element 142 is also disposed at a position similar to that of the aperture 42.

In the above-described configuration, the light amounts received by the light receiving elements 142 are reduced compared to those in the first exemplary embodiment. However, since the light receiving element 142 is also disposed at a position similar to that of the aperture 42, missing of data is suppressed. Other operations are similar to those in the first exemplary embodiment.

Seventh Exemplary Embodiment

An example of an inspection apparatus according to a seventh exemplary embodiment of the present invention is described with reference to FIG. 13B. The same elements or the like as those in the first exemplary embodiment are denoted by the same reference signs and description thereof is omitted. Most of the following description is devoted to points different from those in the first exemplary embodiment.

Figure 13B:
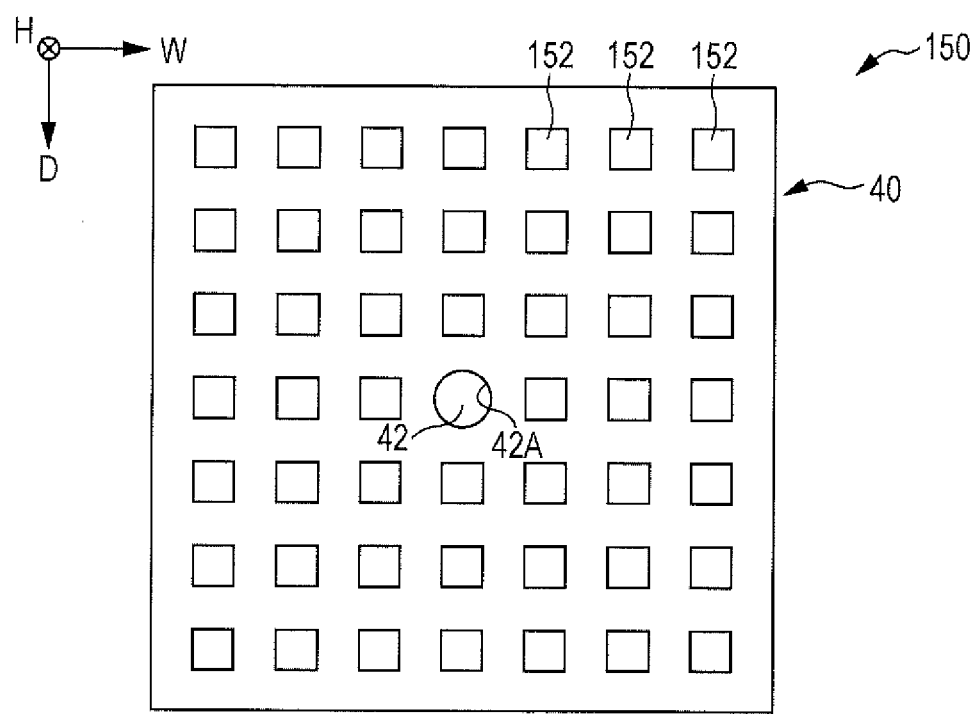

As illustrated in FIG. 13B, light receiving elements 152 that each serve as an example of the light receiving device used in an inspection apparatus 150 according to the seventh exemplary embodiment are arranged at positions in the apparatus width direction and the apparatus depth direction except for a position where the aperture 42 of the stop member 40 is formed.

In the above-described configuration, the number of the light receiving elements 152 that receive the reflected light beam is increased compared to that in the first exemplary embodiment. Thus, inspection capability is improved. Other operations are similar to those in the first exemplary embodiment.

Although the specific exemplary embodiments according to the present invention have been described in detail, the present invention is not limited to these exemplary embodiments. Obviously, practitioners skilled in the art understand that a variety of other embodiments are possible without departing from the scope of the present invention. For example, although it is not particularly described in the aforementioned exemplary embodiments, sequential emission of plural light beams from the light sources 12 may be realized with vertical cavity surface emitting lasers (VCSELs), digital light processing (DLP), a digital micromirror device (DMD), light emitting diodes (LEDs), or the like, or may be realized with a display device such as a liquid crystal display.

Although it is not particularly described in the aforementioned exemplary embodiments, the light beams of plural wavelengths may be selectively emitted from the light sources 12. This allows the reflection characteristics to be inspected for each wavelength.

Although it is not particularly described in the aforementioned exemplary embodiments, the light beams emitted from the light sources 12 may be visible light. In this case, the inspection range may be visually recognized.

Although it is not particularly described in the aforementioned exemplary embodiments, light sources for inspection and light sources that emit visible light for visually recognizing the inspection range may be separately provided and selectively used. In this case, it is desirable that selection of the light source be performed by a half mirror or angle control of DLP.

Although it is not particularly described in the aforementioned exemplary embodiments, unnecessary parts of the lens element 32 and the lens element 34, the unnecessary parts being parts where the light beam does not pass, may be removed. This allows the size of the inspection apparatus to be reduced.

Although it is not particularly described in the aforementioned exemplary embodiments, the light receiving elements may use components such as, for example, photodiodes (PDs), position sensitive detectors (PSDs), or a charge-coupled device (CCD).

Although it is not particularly described in the aforementioned exemplary embodiments, in order to remove ambient light from the light beam received by the light receiving elements, a filter may be provided between the light receiving elements and the lens element 34. With this configuration, out of light beams of various wavelengths, the light beams of a wavelength emitted from the light sources are selected to pass through the filter. This may suppress passage of light of other wavelengths. When the filter is not provided, the ambient light may be removed by the following method: the light receiving elements are caused to receive the light beam when the light sources 12 are turned on and when the light sources 12 are turned off so as to measure a change in the light amount of the received light beam.

Although it is not particularly described in the aforementioned exemplary embodiments, the position of the light sources 12 in the apparatus up-down direction may be changed in order to change the level where the light beams radiated from the light sources to the inspection object OB are condensed. Furthermore, in order to change the level where the light beams radiated to the inspection object OB are condensed from inspection region to inspection region of a single inspection object OB, plural light sources may be disposed at different positions in the apparatus up-down direction. This is effective for minimizing the spot diameter of the light beams radiated to the inspection regions when the inspection object OB has a three-dimensional shape.

Although it is not particularly described in the aforementioned exemplary embodiments, the light receiving elements may receive light through slits or a lens.

Although the degree of irregularity of the inspection object OB is inspected by the inspection apparatus in the aforementioned embodiments, grain, embossing, surface roughness, surface defect, adhesion of foreign matter, or the like of the inspection object OB may be inspected.

Although it is not particularly described in the aforementioned exemplary embodiments, when the surface of the inspection object OB is partly inclined, by comparing the light receiving elements 16 that receive the maximum output of the reflected light at inspection regions, the angle of the inclination may be estimated.

Although it is not particularly described in the aforementioned exemplary embodiments, in the case where the inspection position is predetermined in the inspection object OB, a single light source 12 may be sufficient.

Although it is not particularly described in the aforementioned exemplary embodiments, in the case where the inspection position is predetermined in the inspection object OB, in order to inspect the light amount of the reflected light reflected at a predetermined angle at the predetermined inspection position, a single light receiving element may be sufficient.

The foregoing description of the exemplary embodiments of the present invention has been provided for the purposes of illustration and description. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An inspection apparatus that inspects an inspection object, the apparatus comprising:
   a light emitting device that emits a light beam;
   a first lens disposed such that an optical axis of the first lens extends in one direction, the first lens changing divergence of the light beam that has been emitted from the light emitting device and passes through the first lens;
   a second lens disposed such that an optical axis of the second lens extends in the one direction, the light beam that has exited the first lens and passes through the second lens being condensed on the inspection object by the second lens;
   a light receiving device disposed between the first lens and the second lens, the light receiving device receiving at least part of the light beam that has exited the second lens, been reflected by the inspection object, and passed through the second lens; and
   an inspection device that detects a reflection characteristic of at least part of the inspection object in accordance with a result of light reception performed by the light receiving device.

2. The inspection apparatus according to claim 1,
   wherein a distance between the light receiving device and the second lens in the first direction is substantially equal to a focal length of the second lens.

3. The inspection apparatus according to claim 1, further comprising:
   a stop device disposed between the first lens and the second lens, the stop device restricting the light beam that has passed through the first lens and to be incident upon the second lens,
   wherein a distance between the stop device and the first lens in the first direction is substantially equal to a focal length of the first lens, and
   wherein a distance between the stop device and the second lens in the first direction is substantially equal to a focal length of the second lens.

* * * * *